United States Patent
Mariella, Jr.

(10) Patent No.: US 9,910,011 B2
(45) Date of Patent: Mar. 6, 2018

(54) ISOTACHOPHORESIS SYSTEM HAVING LARGER-DIAMETER CHANNELS FLOWING INTO CHANNELS WITH REDUCED DIAMETER AND WITH SELECTABLE COUNTER-FLOW

(75) Inventor: Raymond P. Mariella, Jr., Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1027 days.

(21) Appl. No.: 13/105,984

(22) Filed: May 12, 2011

(65) Prior Publication Data
US 2012/0175258 A1 Jul. 12, 2012

Related U.S. Application Data

(60) Provisional application No. 61/432,044, filed on Jan. 12, 2011.

(51) Int. Cl.
G01N 27/447 (2006.01)

(52) U.S. Cl.
CPC .............. *G01N 27/44773* (2013.01)

(58) Field of Classification Search
CPC ................... G01N 27/447–27/44795
USPC ............ 204/450–470, 546–550, 600–621, 204/641–645
See application file for complete search history.

(56) References Cited

U.S. PATENT DOCUMENTS

| | | | |
|---|---|---|---|
| 3,384,564 A | | 5/1968 | Ornstein et al. |
| 4,459,198 A | * | 7/1984 | Mizuno et al. ............... 204/602 |
| 4,816,123 A | | 3/1989 | Ogan et al. |
| 7,494,577 B2 | | 2/2009 | Williams et al. |
| 2010/0084271 A1 | | 4/2010 | Santiago et al. |

OTHER PUBLICATIONS

S. Chen, M., Lee, Automated Instrumentation for Comprehensive Isotachophoresis-Capillary Zone Electrophoresis, 2002, Anal. Chem., 72, 816-820.*

Supreet S. Bahga, et al. "High-Sensitivity Detection Using Isotachophoresis with variable Cross-Section Geometry". Electrophoresis 2011, 32, 563-572.

\* cited by examiner

*Primary Examiner* — Bach T Dinh
(74) *Attorney, Agent, or Firm* — Eddie E. Scott

(57) ABSTRACT

An isotachophoresis system for separating a sample containing particles into discrete packets including a flow channel, the flow channel having a large diameter section and a small diameter section; a negative electrode operably connected to the flow channel; a positive electrode operably connected to the flow channel; a leading carrier fluid in the flow channel; a trailing carrier fluid in the flow channel; and a control for separating the particles in the sample into discrete packets using the leading carrier fluid, the trailing carrier fluid, the large diameter section, and the small diameter section.

2 Claims, 10 Drawing Sheets

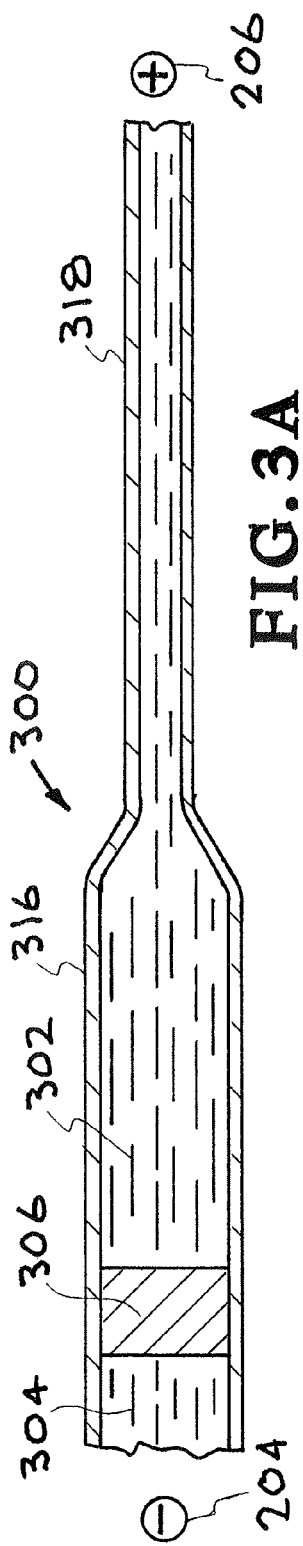
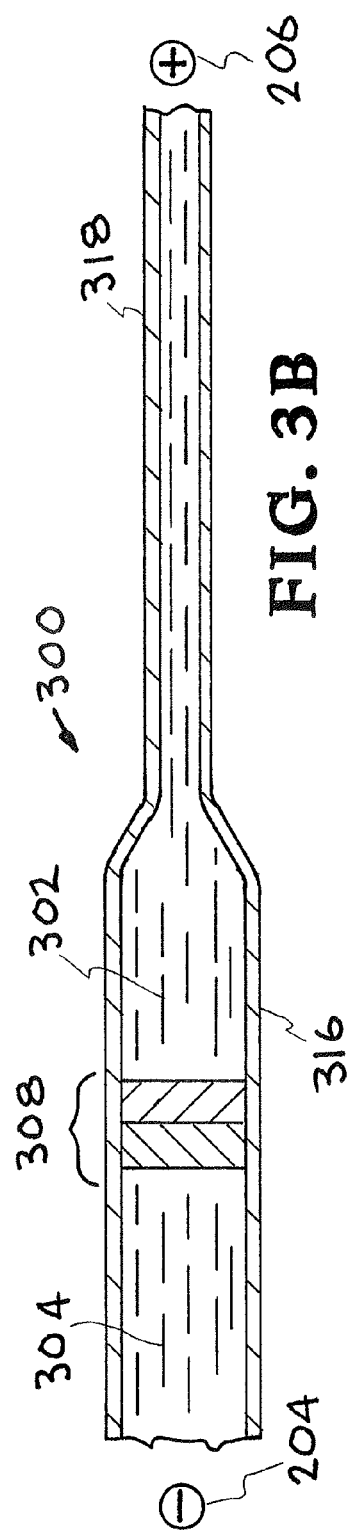
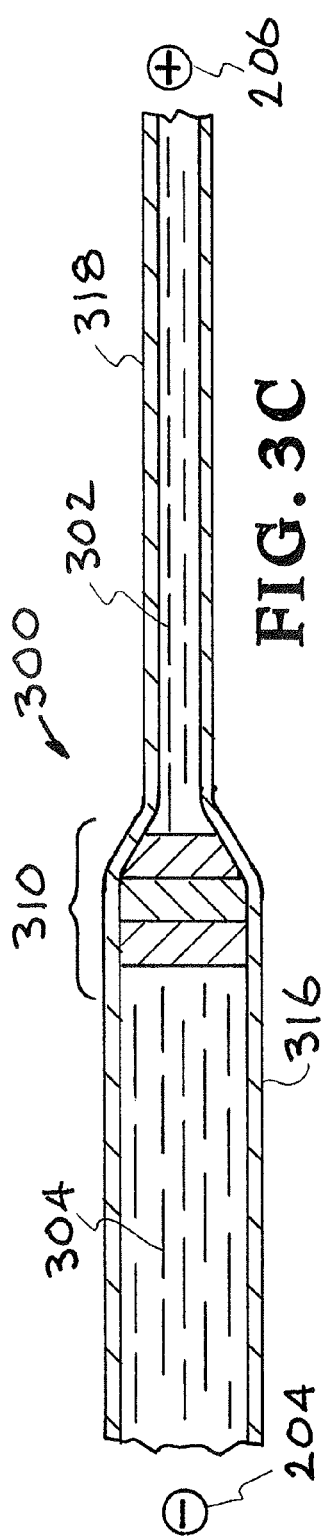

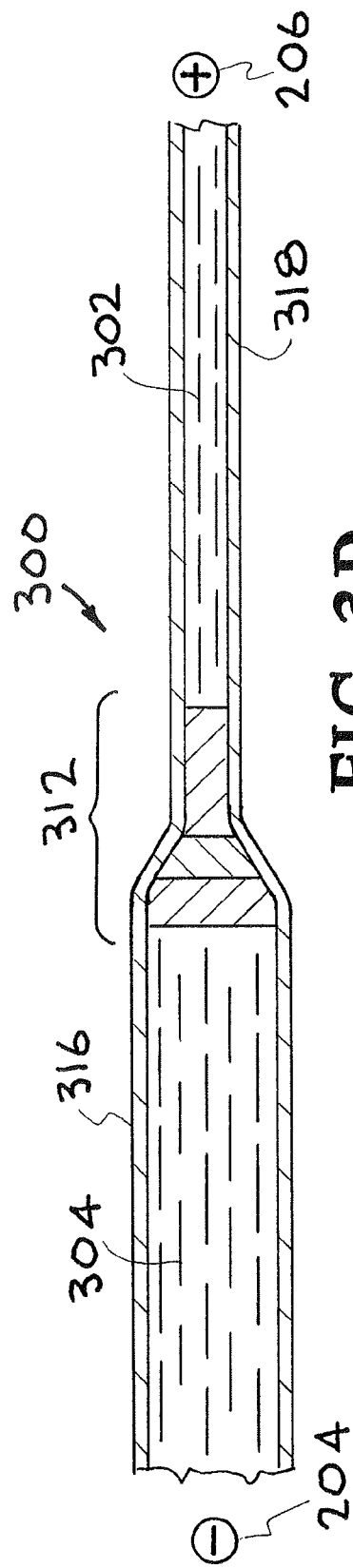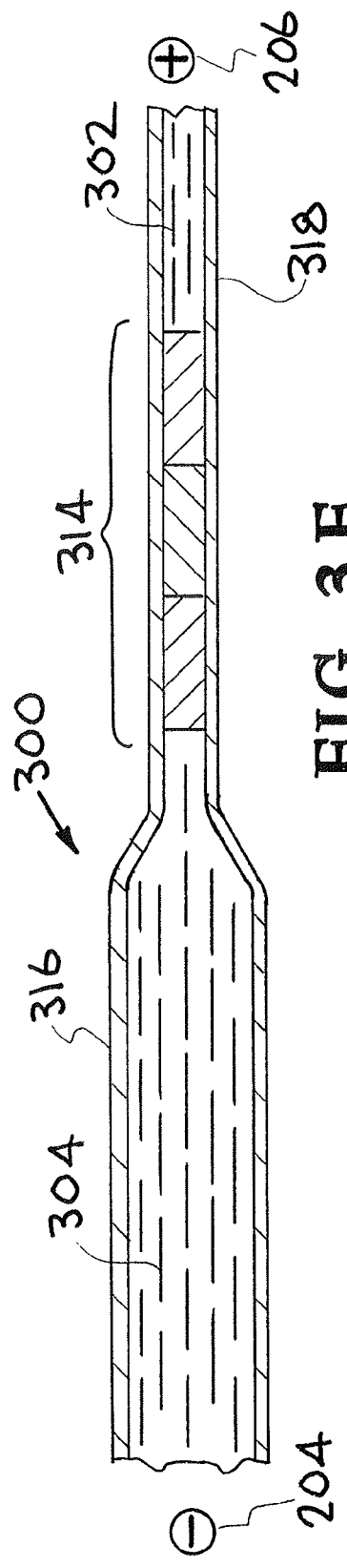

ISOTACHOPHORESIS SYSTEM HAVING LARGER-DIAMETER CHANNELS FLOWING INTO CHANNELS WITH REDUCED DIAMETER AND WITH SELECTABLE COUNTER-FLOW

CROSS-REFERENCE TO RELATED APPLICATIONS

The present application claims benefit under 35 U.S.C. § 119(e) of U.S. Provisional Patent Application No. 61/432,044 filed Jan. 12, 2011 entitled "Isotachophoresis System Having Larger-Diameter Channels Flowing Into Channels With Reduced Diameter And With Selectable Counter-Flow," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to isotachophoresis and more particularly to a staged isotachophoresis system in which larger-diameter channels flow into one or more sequential channels with reduced diameter.

State of Technology

United States Published Patent Application No. 2010/0084271 for control of chemical reactions using isotachophoresis provides the state of technology information described below.

"In the present approach, isotachophoresis (ITP) is exploited to control various aspects of chemical reactions. In ITP, a sample of one or more analytes is typically introduced between a leading electrolyte (LE, containing a leading ion) and a trailing electrolyte (TE, containing a trailing ion). The leading ion, trailing ion and sample components all have the same charge polarity, (i.e., are all anions or cations). Typically, the sample components have effective electrophoretic mobility less than that of the leading ion, but greater than that of the trailing ion. Initially, the sample can be mixed with the LE, with the TE, between the LE and TE, or with both the LE and TE. On application of an electric potential to this system, sample components migrate toward the region between the LE and TE. Typically, these sample ions then form discrete contiguous zones of analyte arranged in order of their (effective) electrophoretic mobilities with the highest mobility nearest the LE. Further details relating to isotachophoresis are described in a text[1] "Isotachophoresis: theory, instrumentation, and applications" by authors Everaerts, F. M., J. L. Beckers, et al., published in Amsterdam and New York by Elsevier Scientific Pub. Co. in 1976, and hereby incorporated by reference in its entirety."

U.S. Pat. No. 7,494,577 for tandem isotachophoresis/zone electrophoresis method and system provides the state of technology information described below.

"Microfluidics is revolutionizing the way activities are performed in a substantial proportion of chemical and physical operations. One area of microfluidics is the manipulation of small volumes of liquids or liquid compositions on a solid substrate, where a network of channels and reservoirs are present. By employing electric fields with electrically conducting liquids, volumes and/or ions can be moved from one site to another, different solutions formed by mixing liquids and/or ions, reactions performed, separations performed, and analyses carried out. In fact, in common parlance, the system has been referred to as "a laboratory on a chip." Various prior art devices of this type include U.S. Pat. Nos. 6,010,608, 6,010,607, 6,001,229, 5,858,195, and 5,858,187 which are a family of applications concerned with injection of sample solutions. See also, U.S. Pat. No. 5,599,432, EPA 0620432, and Verheggen et al., J. of Chromatography 452 (1988) 615-622.

In many of the operations, there is an interest in electrophoretically separating multiple sample components contained in dilute samples, e.g., samples with concentrations of sample components in the femtomolar to nanomolar range. Efficient electrophoretic injection of dilute samples frequently results in large sample volumes and poor resolution of the sample components.

It would thus be desirable to provide an electrophoretic system for improved separation and resolution of sample components, particularly where the sample components are present at nanomolar concentrations or less. It would be further desirable to provide a method of adjusting separation conditions as to maximize electrophoretic separation and resolution."

Normal electrophoretic injection and separations start with the injection of a physically limited sample ["as small as possible," typically determined by the limiting sensitivity of the detection system], containing either ions or charged particles, or both, that is phoresed [transported] along the channel due to an externally-applied voltage. In SSSEP/ITP, The sample is not injected in isolation, but rather there is continuous injection of electrolytes, beginning with a leading electrolyte, which is then followed by injection of the sample, which is then followed by injection of the terminating electrolyte. In traditional EP, the physical extent of the injected sample breaks up into separate components from the original injection under that action of the externally-applied electric field, each component of which migrates according to its electrophoretic mobility as in speed of migration=$\mu E$. Each component also undergoes a physical spreading beyond the limits of size of the injected sample, according to diffusion and other dispersing phenomena, such as inhomogeneities in the media and/or apparatus. Because of the effects of diffusion, no concentration of any component within the originally-injected sample can occur.

The article, "High-sensitivity detection using isotachophoresis with variable cross-section geometry," by Supreet S. Bahga, Govind V. Kaigala, Moran Bercovici, and Juan. G. Santiago in *Electrophoresis* 2011, 32, 563-572 (February 2011) provides the state of technology information described below. The disclosure of the article, High-sensitivity detection using isotachophoresis with variable cross-section geometry," by Supreet S. Bahga, Govind V. Kaigala, Moran Bercovici, and Juan. G. Santiago in *Electrophoresis* 2011, 32, 563-572 (February 2011) is incorporated herein in its entirety for all purposes by this reference.
1.1 General Aspects
Isotachophoresis (ITP) is an electrophoretic separation and preconcentration technique widely applied to food analysis, genetics, pharmacology and toxin detection 1, 2. In ITP, analytes simultaneously focus and can separate between a high effective mobility leading electrolyte (LE) ions and low effective mobility trailing electrolyte (TE) ions. When present in sufficient amount, the analytes focus and segregate into distinct, contiguous zones with locally uniform (plateau-like) concentrations 3. However, when analytes are present in trace quantities, they focus into peaks of width determined by the diffusive interface between neighboring zones. These two regimes are respectively termed as "plateau mode" and "peak mode" ITP 4, 5. Several adjacent analytes in peak mode are practically indistinguishable from each other.

1.4 Analytical Relations and Scaling Arguments for Varying Cross-Sectional Area Channels We use the model presented in Section 1.3 to derive analytical relations for the dependence of plateau zone length and detection time on channel geometry and buffer chemistry. Consider the separation channel in FIG. 1B, consisting of a large cross-section region with area $A_L$, followed by a smaller cross-section region with area $A_D$. In ITP with semi-infinite injection, the analyte primarily accumulates in the large cross-section channel, which we refer to as the "loading section." This accumulation is often in peak mode. The analyte zone then reaches the small cross-section channel and expands axially along the channel, resulting in a newly created plateau or plateau with larger zone length. To achieve higher sensitivity, the analyte is detected in this smaller cross-section channel, which we will refer to as the "detection section." The zone length, $\Delta_P$, is obtained by solving Eq. (5). Assuming negligible EOF, Eq. (5) can be written as, $$\frac{dy}{dx} = \frac{\mu_{t,T} \sigma_L}{\mu_{l,L} \sigma_T} \frac{A(x)}{A(y)}, \quad (6)$$

which describes the relative motion of the trailing interface to the leading interface. For a varying cross-section channel with large cross-section followed by small cross-section region (each section with uniform area) as in FIG. 1B, Eq. (6) can be solved to obtain, $$\int_0^{L_L} A(y)dy = \frac{\mu_{t,T} \sigma_L}{\mu_{l,L} \sigma_T} \int_0^{L_L + \Delta_P} A(x)dx \quad (7)$$

$$A_L L_L = \frac{\mu_{t,T} \sigma_L}{\mu_{l,L} \sigma_T} (A_L L_L + A_D \Delta_P)$$

Rearranging this expression, we obtain an expression for zone length, $\Delta_P$, in terms of channel geometry and electrolyte chemistry, $$\Delta_P \left( \frac{\mu_{l,L}}{\sigma_L} - \frac{\mu_{t,T}}{\sigma_T} \right) \left( \frac{A_L L_L}{A_D} \right) \frac{\sigma_T}{\mu_{t,T}}. \quad (8)$$

Next, we apply the jump conditions (4) across the TE-to-analyte interface and define $V_{ITP} = \mu_{a,A} J/\sigma_A = \mu_{t,L} J/\sigma_L$, where $V_{ITP}$ is the velocity of the LE-to-analyte interface. Thus, the parenthetic mobility term on the right-hand-side of (8) can be written explicitly in terms of analyte concentrations:

$$\left( \frac{\mu_{l,L}}{\sigma_L} - \frac{\mu_{t,T}}{\sigma_T} \right) - (\mu_{a,T} - \mu_{t,T}) \frac{c_{a,T}}{\sigma_T c_{a,A}} \quad (9)$$

The concentration of analyte in the adjusted TE zone, $c_{a,T}$, can then be related to its concentration in the well using the jump conditions across the stationary interface of TE well and adjusted TE, $$\frac{\mu_a^0}{\sigma^0} c_a^0 = \frac{\mu_{a,T}}{\sigma_T} c_{a,T}. \quad (10)$$

where the superscript describes a property evaluated at the well. Combining expressions (8)-(10) we obtain an explicit dependence of zone length on the concentration of the analyte in the TE well and on channel geometry, $$\Delta_P = \left( 1 - \frac{\mu_{t,T}}{\mu_{a,T}} \right) \frac{\mu_a^0}{\mu_{t,T}} \frac{\sigma_T}{\sigma^0} \left( \frac{A_L L_L}{A_D} \right) \frac{c_a^0}{c_{a,A}}. \quad (11)$$

This shows that the plateau zone length of an analyte, $\Delta_P$, is proportional to both the concentration of the analyte in the well, $c_a^0$, and to the geometric parameter $A_L L_L/A_D$. This geometric parameter is equivalent to the total length of a uniform cross-section channel (irrespective of cross-sectional area or applied current), which would have been required to obtain the same zone length. We therefore refer to $A_L L_L/A_D$ as the "effective length" of the variable-area channel, and denote it by $L_{eff}$. For a given chemistry, the zone length, $\Delta_P$ therefore scales as, $$\Delta_P \propto L_{eff} c_a^0, \quad (12)$$

$$L_{eff} = \frac{A_L L_L}{A_D}.$$

Resource limits on applied voltage and/or applied current influence the dynamics since they directly affect the detection time. For example, the miniaturized ITP device of 10 had a voltage limited to 200 V (currently, this device has a limit of 350 V). To derive an appropriate scaling for the detection time in such systems, we here neglect EOF, and solve for the location of the front interface with Eq. (5), $$\frac{dt}{dx} = \frac{\sigma_L A(x)}{\mu_{l,L}} \frac{\Delta V}{R(x)}. \quad (13)$$

Here R denotes the electrical resistance of the channel. The resistance of the channel increases during ITP, as high-conductivity LE is replaced by a lower conductivity TE. Since the analyte zone is typically much smaller than the overall channel length, we here neglect its contribution to the channel resistance. With this assumption we show in the Supporting Information that the detection time, T, can be approximated as $$T \approx \frac{L_L L_D}{\mu_{l,L} \Delta V} \left( \frac{A_L}{A_D} + \frac{1}{2} \left( 1 + \frac{\sigma_L}{\sigma_T} \right) \frac{L_L}{L_D} \right). \quad (14)$$

The two analytical expressions (12) and (14) enable simple evaluation of the advantages of using variable cross-section channels over uniform cross-section channels. For example, if we take $A_L/A_D=10$, $L_L=L_D=L$, $\sigma_L/\sigma_T=10$, then from Eq. (12) the effective length is $L_{eff}=10L$. This means that in order to obtain same zone length, a uniform cross-section channel would require a 10-fold longer channel. Furthermore, using Eq. (14), one can show that the detection time using the variable cross-section geometry is 35-fold shorter than that of a longer channel with uniform cross-section and actual length equal to $L_{eff}$ ($L_L=L_{eff}$, $L_D=0$). This example shows that variable cross-section channels not only results in higher sensitivity compared to fixed cross-section channels, but also in significantly shorter detection times for fixed plateau widths.

Theoretical plateau widths are directly relevant to sensitivity of the assay. For example, a good working definition for the sensitivity limit is when the theoretical plateau width is significantly larger (say twice or more) than the interface width caused by diffusion and advective dispersion (see Khurana and Santiago 9 for further discussion). Plateau zone lengths are independent of applied voltage or current (see Eq. 11). However, in the absence of advective dispersion 9, interface thickness is inversely proportional to the electric field in the channel 23. Thus, the interface thickness (and SNR) show different dependence on channel geometry for constant voltage and constant current operation.

The trade-offs of assay time, SNR, channel area ratio, applied voltage and applied current are discussed in detail in the Supporting Information, and summarized here. For fixed voltage operation, increasing cross-section ratio results in larger zone length, higher electric field and sharper interfaces. Therefore, SNR improves significantly by increasing the cross-section ratio. Whereas, increasing length of the loading section increases the zone length but leads to lower electric field and thicker interfaces. Thus, SNR does not improve significantly by increasing the length of loading section. For a fixed voltage and channel length, SNR can be increased by increasing the cross-sectional area ratio, but at the expense of longer assay time.

In contrast, for fixed current operation, electric field and interface thickness in the detection section do not depend on the dimensions of the loading section. Therefore, significant improvements in SNR can be obtained by increasing both cross-section ratio and loading length, which give larger zones and sharper zone boundaries. For both fixed current and channel length, SNR can be increased by decreasing the area of detection section ($A_D$), without increasing the assay time.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Isotachophoresis, also known by numerous alternative names, is an electrophoretic technique that stacks mixtures of two or more ions [or charged particles] in solution, according to their electrophoretic mobilities, $\mu_i$, where the subscript "I" refers to the "$i^{th}$" ion. The ultimate resolution of two ions, "j" and "k" is a non-linear function of the differences of their electrophoretic mobilities, $\mu_j$ and $\mu_k$ as well as their diffusion coefficients in the solution at the interface between the separated regions. Absent a counter-flow, the ions are transported along any separation channel by the electric field E; this means that if more time were required to attain the ultimate separation, which would accompany the use of a larger sample, for example, then a longer separation channel would be required for any given E. The present invention provides a system through which the overall time can be reduced to separate any given sample volume and also a system through which a reduced length of channel can be utilized, which increases the portability of the separation system. The reduction in overall time is achieved with the use of a narrowing taper of the channel cross section and the reduction of overall channel length can be achieved with the use of a counter flow.

The present invention provides an isotachophoresis system for separating a sample containing particles into discrete packets including a flow channel, the flow channel having a large diameter section and a small diameter section; a negative electrode operably connected to the flow channel; a positive electrode operably connected to the flow channel; a leading carrier fluid in the flow channel; a trailing carrier fluid in the flow channel; and a control for separating the particles in the sample into discrete packets using the leading carrier fluid, the trailing carrier fluid, the large diameter section, and the small diameter section. The present invention has use in analysis of particles.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 3A through E illustrated a series of figures that show what takes place in a reducing flow channel.

DETAILED DESCRIPTION OF SPECIFIC EMBODIMENTS

Figure 1:
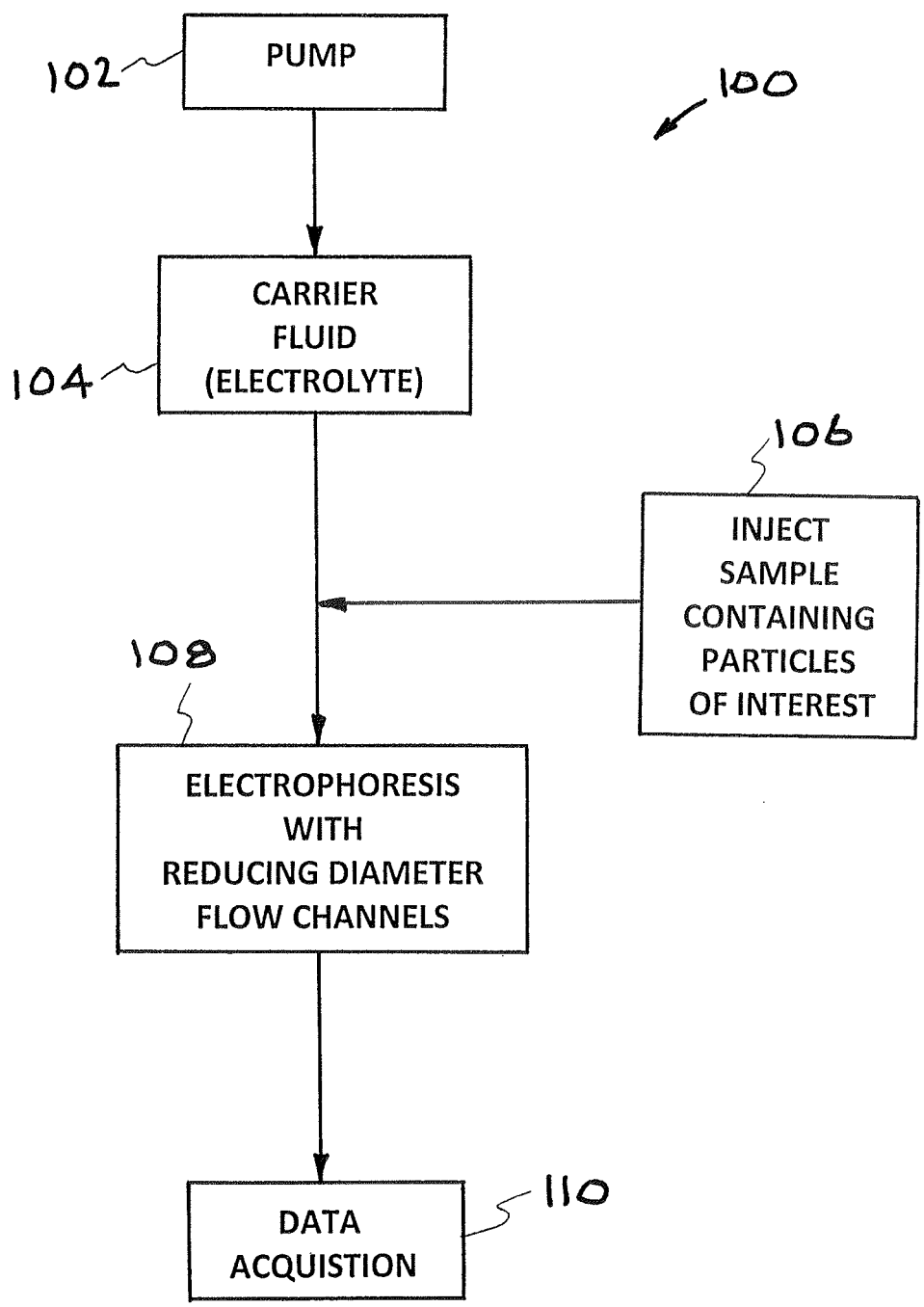
FIG. 1 is a flow chart of illustrating an electrophoresis system with reducing diameter flow channel (ESRD).

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a staged isotachophoresis system in which larger-diameter channels flow into one or more sequential channels with reduced diameter. This provides the ability to isolate a species into a better detectable band. This is particularly advantageous when the analytes of interest includes minority constituents in the mixture and possess electrophoretic mobilities that differ from the majority constituents of the mixture.

For example, if one is interested in detecting a trace of actinides that have been dissolved along with a portion of limestone [$CaCO_3$], the $Ca^{2+}$ ions will migrate at a much higher rate than the actinides and a leading electrolyte may be selected that would allow the $Ca^{2+}$ to escape, thus significantly reducing the overall volume of the sample for analysis. One could use $Na^+$ or $Mg^{2+}$ as leading electrolytes, for example, which would prevent the actinides from phoresing out of the sample but would allow the $Ca^{2+}$ to escape.

When in contact with strongly acidic solutions, glass or quartz surfaces become positively charged. In neutral or basic solutions, the surface would become negatively charged. The overall rate of plug flow due to electroosmotic pumping is $$v = \in \in_0 \zeta E_z / \mu \quad \text{(Equation 1)}$$

where $\in_0$ and $\in$ are the electrical permittivity of vacuum and the dielectric constant of the solution, respectively, $\zeta$ is the zeta potential of the solid surface, $\mu$ is the solution viscosity, and $E_z$ is the electric field strength.

The term isotachophoresis, as used in this patent application, means: "a technique in analytical chemistry used to separate charged particles. It is a further development of electrophoresis. It is a powerful separation technique that uses a self-forming, discontinuous electrical field to create sharp boundaries between the sample constituents."

Isotachophoresis is sometimes referred to as: "Disc electrophoresis," or "displacement electrophoresis," or "steady-state-stacking electrophoresis." In isotachophoresis the sample is introduced between a fast leading electrolyte and a slow terminating electrolyte. After application of an electric potential a low electrical field is created in the leading electrolyte and a high electrical field in the terminating electrolyte. The pH at sample level is determined by the counter-ion of the leading electrolyte that migrates in the opposite direction. In the first stage the sample constituents migrate at different speeds and start to separate from each other. The faster constituents will create a lower electrical field in the leading part of the sample zone and vice versa. Finally the constituents will completely separate from each other and concentrate at an equilibrium concentration, surrounded by sharp electrical field differences.

The Physics of charge neutrality for a single conductor requires that the current be the same throughout the length of the conductor, which, for electrophoresis translates into $$j = E_{LE}\kappa_{LE} = E_{TE}\kappa_{TE} = E_A\kappa_A = E_B\kappa_B = \ldots = E_i\kappa_i \quad \text{[Equation 2]}$$

where $\kappa$ is the specific conductivity given by the product of Faraday constant and the sum of product of concentration $c_i$, charge $z_i$, and mobility $\mu_i$ of $i^{th}$ species; that is $$\kappa_i = c_i * z_i * \mu_i \quad \text{[Equation 3]}$$

The equation, above, for current density for a single conductor can be re-cast as Ohm's law, which distributes the total applied voltage according to the resistance of each electrolyte, in an analogous way to a series of resistors, with the voltage drop across any electrolyte being directly proportional to its resistance; that is E=IR. For any unit length of an electrolyte, the resistance=$1/(\kappa_i * A)$; that is, the resistance and, hence, voltage drop along any unit length of electrolyte is inversely proportional to its specific conductance and to the cross-sectional area of the electrolyte, which would normally be defined by the inner diameter of the confining channel. This means that a smaller-diameter channel, when in series with a larger-diameter channel, will tend to have a larger voltage drop per unit length than the larger-diameter channel. This may be viewed as a detrimental property of following an initial larger-diameter ITP separation with a narrower-diameter portion, since the time to traverse a length of narrower channel under a constant-current drive will inherently be less than that of a wider channel, but the pre-stacking that is performed by the larger-diameter portion will inherently increase the performance of the narrower portion, if the latter had simply been "stand-alone."

There is another approach that can mitigate the possible lack of time for equilibration in a narrower channel that follows a wider channel—the use of counter-flow. If advantageous, for example if one desired to minimize the total physical length of the separation channels, one could use two rates of counter flow, with a higher overall volumetric flow while the sample was in the larger channel and a lower counter flow when admitting the sample to phorese into the narrower channel. The goal would be to retard the overall phoresis of the entire sample long enough to allow achievement of a steady-state distribution of species in the wider channel, stacked according to their electrophoretic mobilities, prior to admitting the sample into the narrower channel for final separation and maximized resolution.

Referring now to the drawings, and in particular to FIG. 1, a flow chart of the electrophoresis system with reducing diameter flow channel (ESRD) is illustrated. The flow chart includes the following components: 100—Electrophoresis system with reducing diameter flow channel (ESRD); 102—Pump, gravity etc.; 104—Carrier fluid, electrolyte, water etc.; 106—sample injection with particles of interest; 108—Electrophoresis with reducing diameter flow channel; and 110—Data acquisition.

The system 100 consists of a pump 102 or some other source such as gravity, etc. etc, for moving fluid through the system 100. There is a reservoir 104 of a carrier fluid, electrolyte is shown but can be water etc. A sample 106 containing particles of interest is injected into the system 100 at 106. The carrier fluid 104 and the injected sample 106 travel to the electrophoresis with reducing diameter flow channels 108 where the particles of interest are separated into discrete packets by the electrophoresis process, When the electrophoresis step is completed, data acquisition 110 takes place.

Figure 2A:
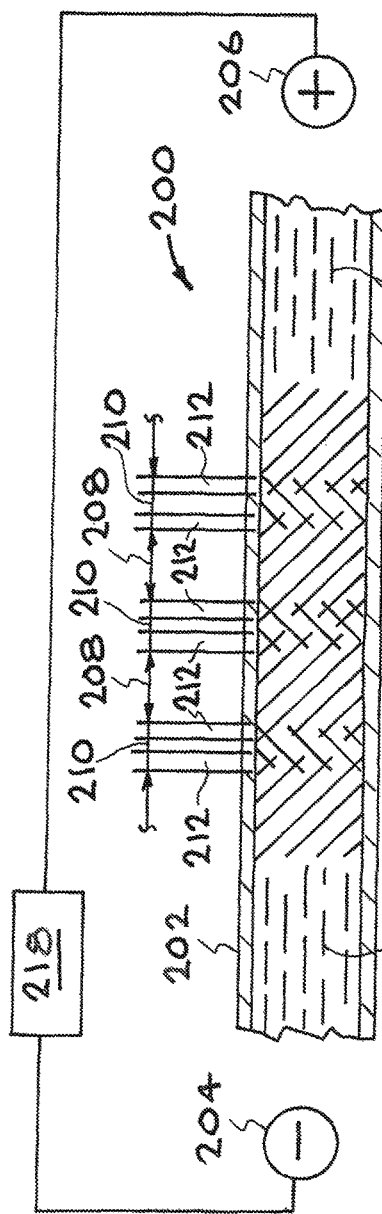
FIG. 2A shows a large diameter flow channel in a tube with the injected sample trapped between the carrier fluids.

Referring now to FIG. 2A. a large diameter flow channel 200 in a tube 202 with the injected sample 106 trapped between the carrier fluid 104 is shown. This is accomplished by starting the flow of the carrier fluid 104 then injecting the sample 106 into the system and continuing the flow of carrier fluid. The large diameter flow channel includes the following components: 200—Large diameter flow channel; 202—Tube; 204—Negative electrode; 206—positive electrode; 208—Area of interest; 210—Area of interest; and 212—Overlap.

In FIG. 2A the injected sample 106 is represented by the cross hatching. Due to the electrophoresis process the particle of interest in the sample 106 will separate into discrete disk like packets in tube 202; however, there will be some overlap between the disk-like packets. This overlap indicated by the numeral 212. Depending on the thickness of the packet of the particles of interest could obscure the area of interest indicated by the numeral 210, other areas 208 are large enough to not be obscured by the overlap 212. Also shown on FIG. 2A are two electrodes, 204 is the negative electrode and 206 is the positive electrode—the electrodes are necessary parts of the electrophoresis process. Also shown on FIG. 2A is a power source 218 that applies an electric potential across the two electrodes 204 and 206. The power source 218 shown in FIGS. 2A and 2B is a necessary part of the electrophoresis process.

Figure 2B:
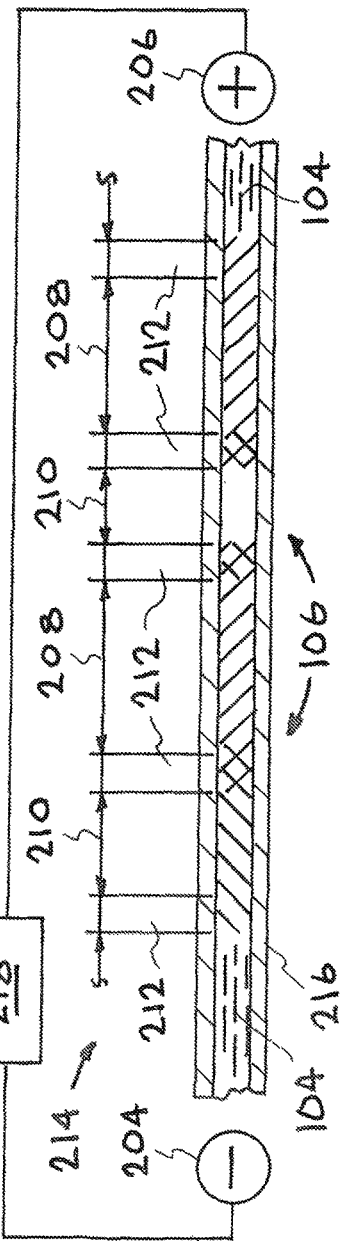
FIG. 2B shows a reduced diameter flow channel in a tube.

FIG. 2B shows a reduced diameter flow channel 214 in a tube 216. The reduced diameter flow channel includes the following components: 214—reduced diameter flow channel and 216—Tube.

The injected sample 106 is again shown trapped between flows of the carrier fluid 104 as in FIG. 2A. The reduced diameter of the flow channel 214 will cause the packets of the particles of interest to stretch out the overlap 212 becomes less critical as the area of interest 210 has now become much larger. Electrodes 204 and 206 are also shown as in FIG. 2A FIGS. 3A through E are a series of figures that will show what takes place in a reducing flow channel. FIGS. 3A through E include the following components: 300—Reducing channel; 302—Leading carrier fluid; 304—Trailing carrier fluid; 306—Mixed sample; and 308—Sample starting to separate.

In FIG. 3A a flow channel 300 is shown with large diameter section 316 and a reduced diameter section 318. In this figure the sample 306 is shown between leading carrier fluid 302 and trailing carrier fluid 304. In this figure the sample 306 is a mixed sample. In FIG. 3B the sample 306 is starting to separate into discrete packets as indicated at 308 as the sample proceeds along the channel. IN FIG. 3C the sample has separated into discrete packets as indicated at 310. The sample is also shown entering the reduced diameter section 318 of the channel. FIG. 3D shows more of the sample has entered the reduced diameter section of the channel and the packets of particles are starting to stretch out, indicated at 312. In FIG. 3E all of the sample has entered the reduced diameter section of the channel and the discrete packets are all stretched out greatly enhancing the ability to gain accurate data.

Figure 4A:
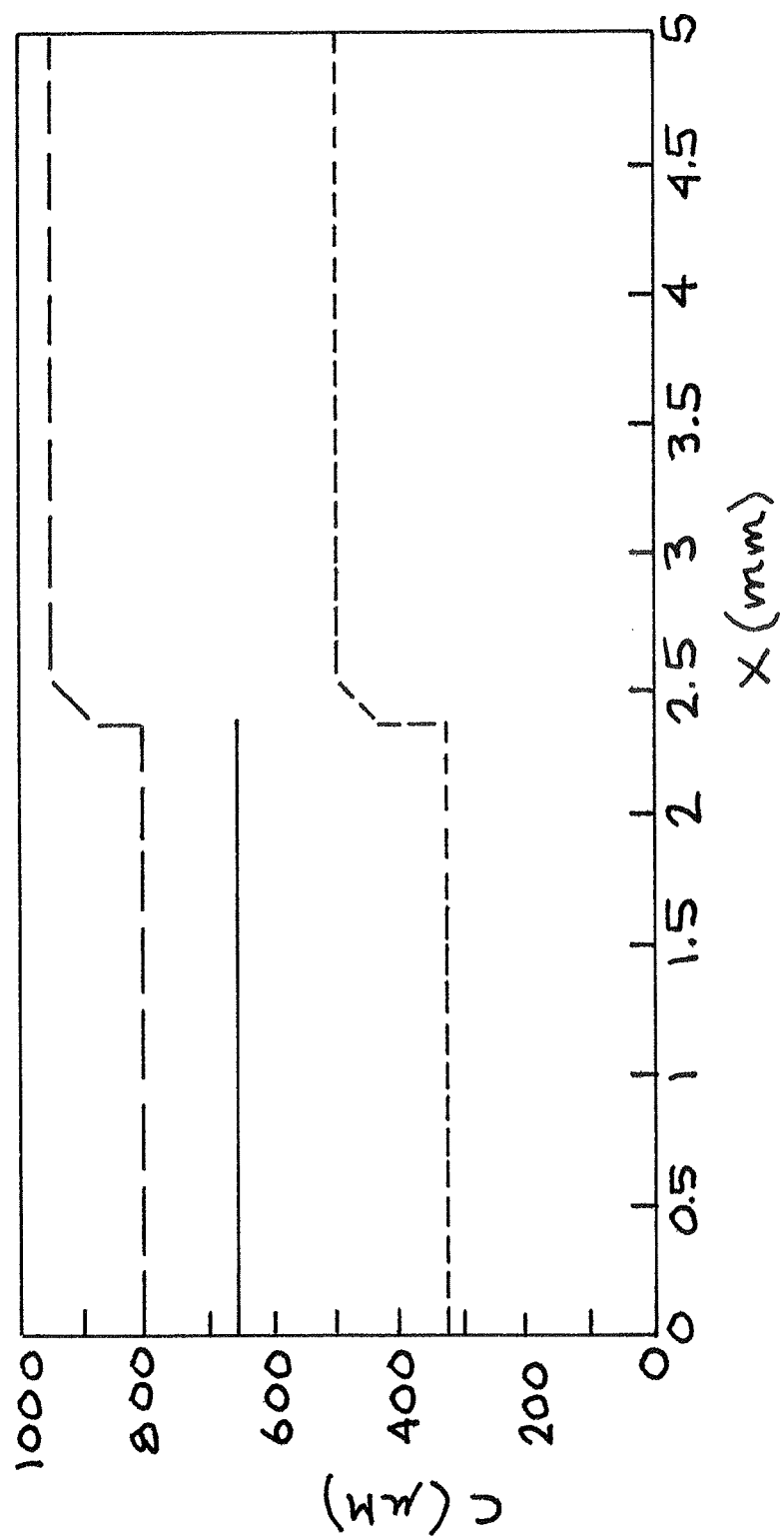
FIG. 4A through 4C show ITP runs of Applicant's development investigations.
Figure 4B:
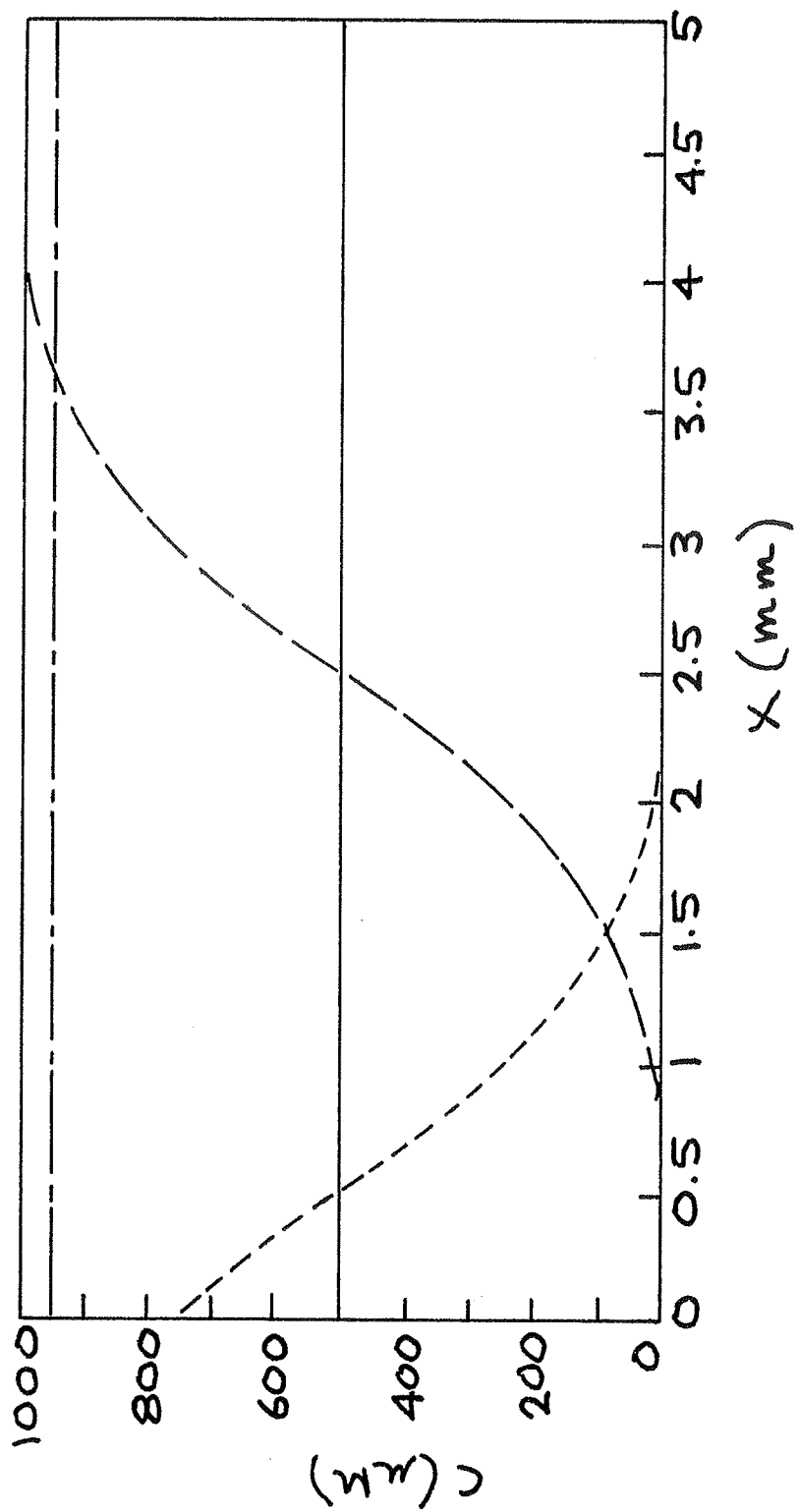
Figure 4C:
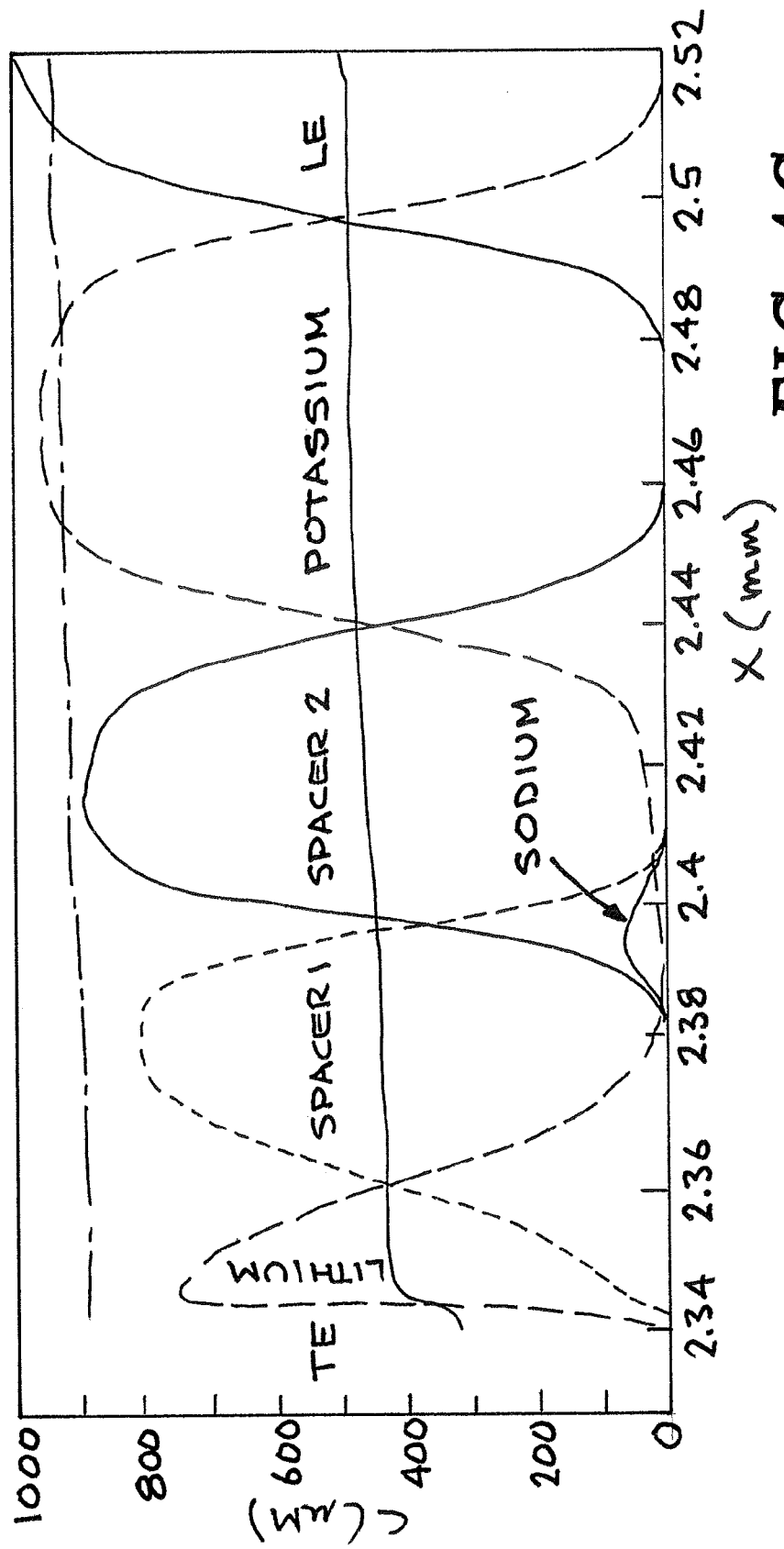

Applicant has conducted development investigations on the present invention. Simulations of two ITP runs, using MatLab code "Spresso®," which is available for download from Stanford University. Each run operates at the same current density [0.5 mA/mm$^2$] and starts with a 0.4-µL volume of analytes: 10-µM concentrations of alkali metals K$^+$ and Li$^+$, with 0.03-µM concentration of Na$^+$, and 8-µM concentration of undefined "spacer" ions. In the first one, the separation column has a cross-sectional area of 0.2 mm$^2$ and the injection length of the sample is 2 mm. In the second case, the separation column has a cross-sectional area of 0.02 mm$^2$ and, hence, the injection length of the sample is 20 mm. In both cases, the leading and trailing electrolytes have a concentration of 0.001 M, 100× higher than that of any of the analytes. Because the concentration of the leading electrolyte largely dictates the final concentration of all analytes, the individual analytes are both purified from each other as well as concentrated. FIG. 4A is a print out from Spresso, showing the starting concentrations of all electrolytes for the case with 0.2-mm$^2$ cross section and a 2-mm injection length—note that on this linear scale, none of the analytes, all injected between 0.5 and 2.5 mm on the x axis, is discernable above the baseline. FIG. 4B shows this same sample, in the moving frame of reference of the interface between the leading electrolyte and the K$^+$ ions, after 1.25 seconds of isotachophoresis. FIG. 4C is an expanded view of the same run, showing the stacking as well as the mostly-resolved separation of K, Li, and the trace amount of Na, all of which, in the absence of the spacer ions, would have been heavily overlapped. The approximate width of the baseline-to-peak transition for each analyte is on the order of 0.03 to 0.04 mm, as determined by the diffusion coefficients and ratio of electrophoretic mobilities with neighboring ions. Again, in this first case, a steady-state stacking arrangement is attained after only 1.25 seconds.

Figure 5A:
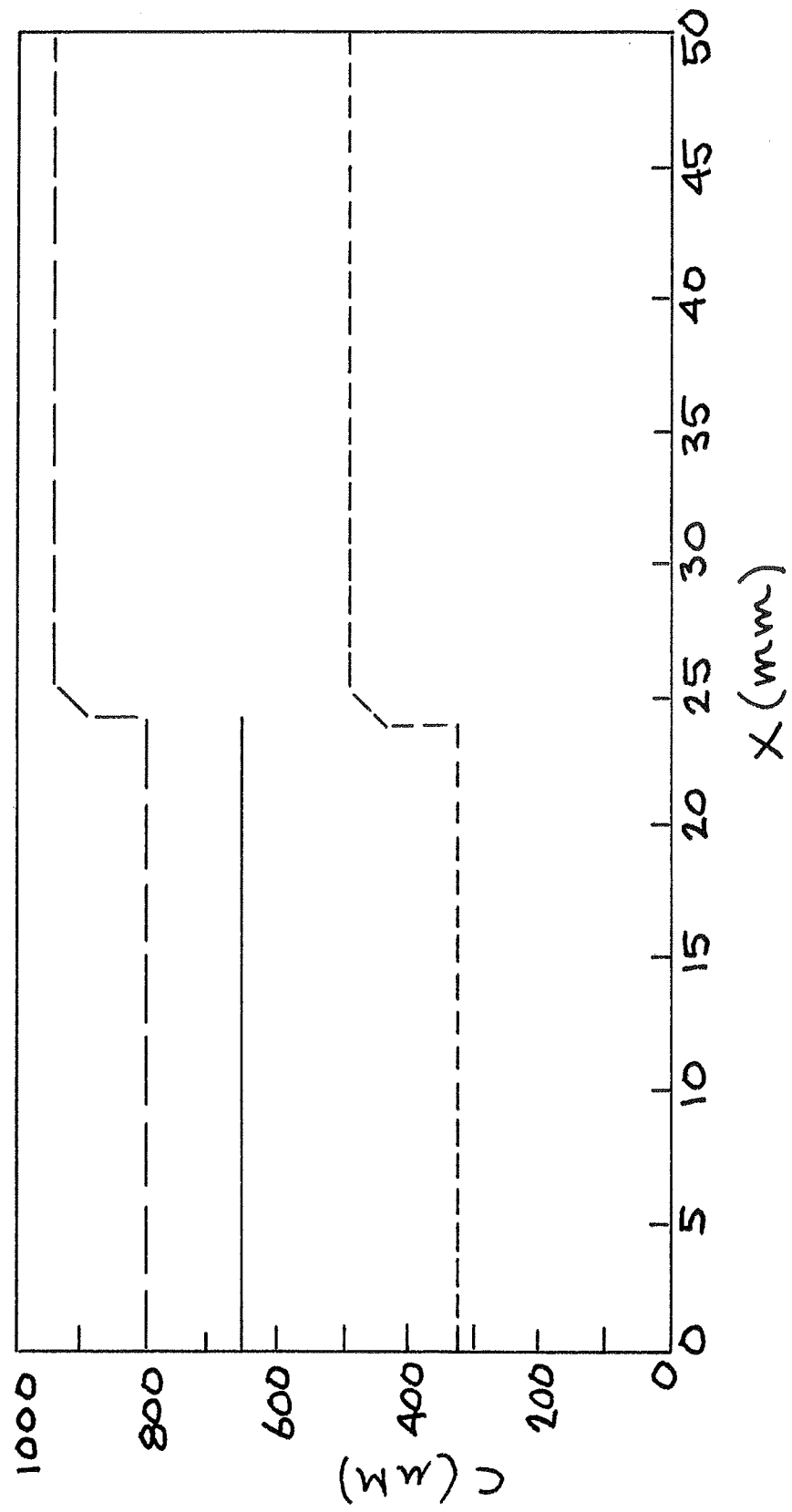
FIG. 5A through 5C show the results of additional development investigations.
Figure 5B:
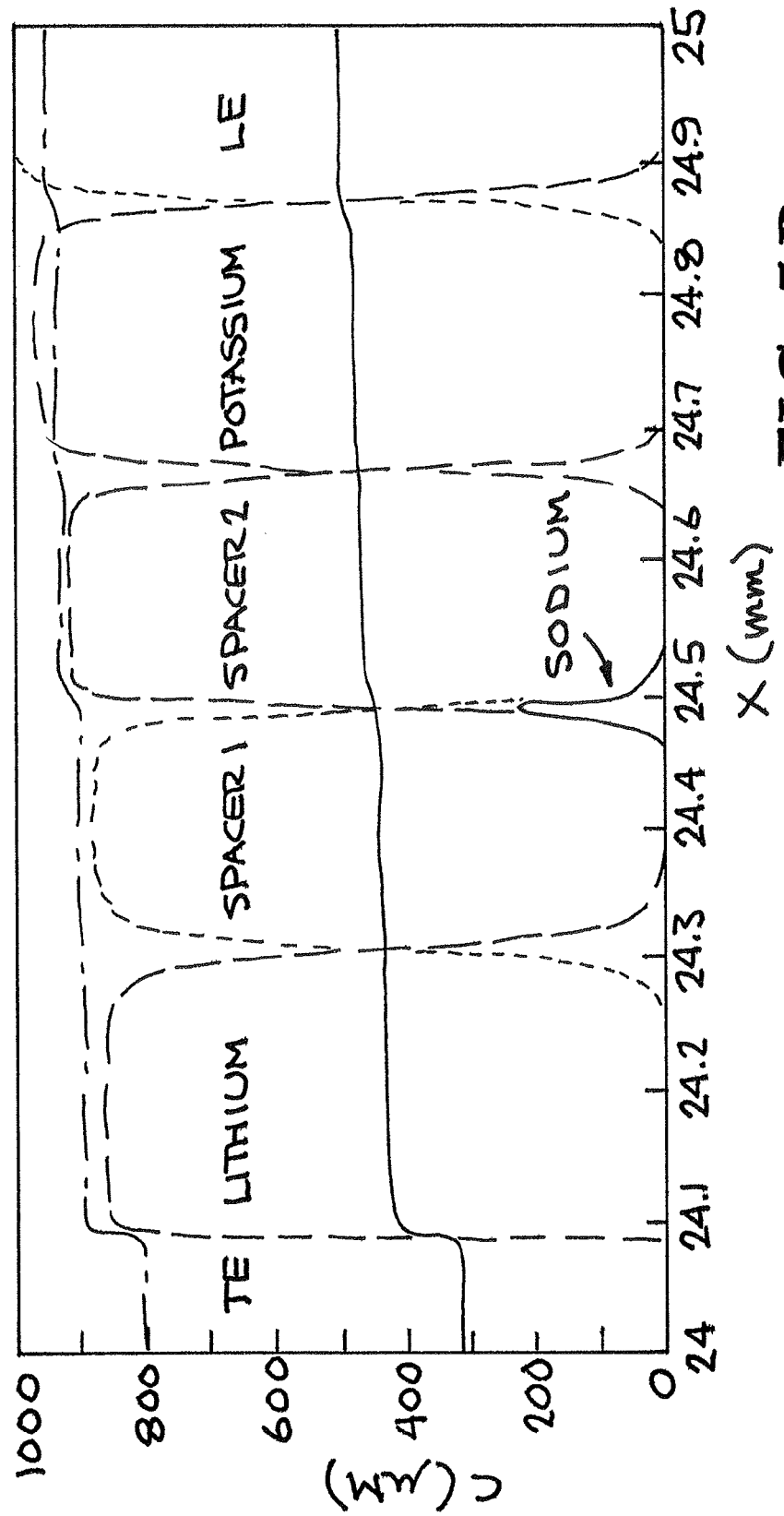
Figure 5C:
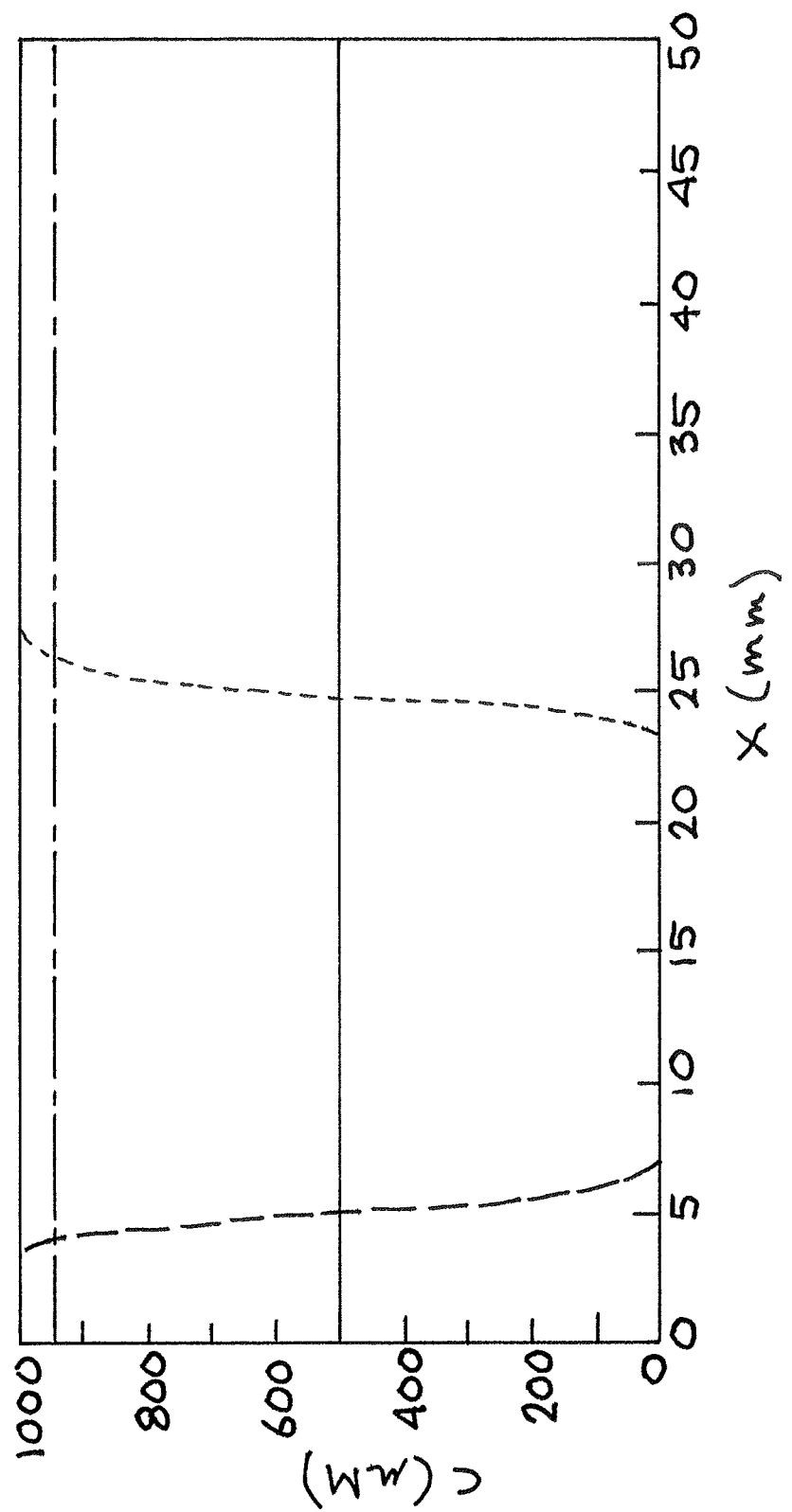

FIG. 5A shows the start of the second case, which starts with a 0.02-mm$^2$ cross-section separation channel and a 20-mm injection length. Again, on this linear scale, none of the analytes, all injected between 5 and 25 mm on the x axis, is discernable above the baseline. FIG. 5B is a plot of concentrations of analytes after 12 seconds of isotachophoresis, and, although it does appear to be similar to what is seen in FIG. 4B, FIG. 5C shows an expanded view of the same time point. Now, the advantage of using a separation channel with smaller cross-sectional area can be clearly seen—the approximate width of the baseline-to-peak transition for each analyte is still on the order of 0.03 to 0.04 mm, but because the length of channel that is occupied by each analyte is approximately 10× larger, the relative overlap between analytes is greatly reduced. There are two "costs" that are associated with the improved separation—the time to attain steady-state stacking is roughly 10× larger and the voltage that is needed to generate the same current density is roughly 10× larger.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An isotachophoresis apparatus consisting of:
   an isotachophoresis housing consisting of
   an isotachophoresis flow channel having
   a large diameter section, said large diameter section providing a leading section with an entrance; and
   a small diameter section, said small diameter section providing a trailing section with an exit;
   a mixed sample in said isotachophoresis flow channel, said mixed sample including first particles and second particles;
   a negative electrode operably connected to said isotachophoresis housing, said negative electrode located at said entrance to said large diameter section;
   a positive electrode operably connected to said isotachophoresis housing, said positive electrode located at said exit of said small diameter section;
   a power source connected to said negative electrode and said positive electrode for applying said electric potential across said negative electrode and said positive electrode;
   a leading carrier fluid in said isotachophoresis flow channel in said isotachophoresis housing;
   a trailing carrier fluid in said flow isotachophoresis channel in said isotachophoresis housing;
   an electric potential applied across said negative electrode and said positive electrode; and a pump for moving said mixed sample including first particles and second particles, said leading carrier fluid, and said trailing carrier fluid in said isotachophoresis flow channel; thereby separating said first particles in said mixed sample into first discrete packets using said leading carrier fluid, said trailing carrier fluid, said large diameter section channel in said isotachophoresis housing, and said small diameter section channel in said isotachophoresis housing; and separating said second particles in said mixed sample into second discrete packets using said leading carrier fluid, said trailing carrier fluid, said large diameter section, and said small diameter section in said isotachophoresis housing.

2. An isotachophoresis method consisting of the steps of:

providing an isotachophoresis housing;

providing an isotachophoresis flow channel in said housing;

providing a large diameter section in said flow channel in said housing, said large diameter section providing a leading section with an entrance;

providing a small diameter section in said flow channel in said housing, said small diameter section providing a trailing section with an exit;

providing a mixed sample in said isotachophoresis flow channel, said mixed sample including first particles and second particles;

providing a negative electrode operably connected to said housing, said negative electrode located at said entrance to said large diameter section;

providing a positive electrode operably connected to said housing, said positive electrode located at said exit of said small diameter section;

providing a leading carrier fluid in said isotachophoresis flow channel in said isotachophoresis housing;

providing a trailing carrier fluid in said isotachophoresis flow channel in said isotachophoresis housing;

providing an electric potential applied across said negative electrode and said positive electrode;

providing a pump for moving said mixed sample including first particles and second particles, said leading carrier fluid, and said trailing carrier fluid in said isotachophoresis flow channel;

using said electrical potential and said pump for separating said first particles in said mixed sample into first discrete packets using said leading carrier fluid, said trailing carrier fluid, said large diameter section, said small diameter section, said negative electrode, and said positive electrode; and using said electrical potential and said pump for separating said second particles in said mixed sample into second discrete packets using said leading carrier fluid, said trailing carrier fluid, said large diameter section, said small diameter section, said negative electrode, and said positive electrode.

\* \* \* \* \*